(12) United States Patent
Böscke et al.

(10) Patent No.: US 11,185,243 B2
(45) Date of Patent: Nov. 30, 2021

(54) SENSOR DEVICE

(71) Applicant: OSRAM Opto Semiconductors GmbH, Regensburg (DE)

(72) Inventors: Tim Böscke, Regensburg (DE); Stephan Haslbeck, Regensburg (DE)

(73) Assignee: OSRAM OLED GmbH, Regensburg (DE)

( * ) Notice: Subject to any disclaimer, the term of this patent is extended or adjusted under 35 U.S.C. 154(b) by 397 days.

(21) Appl. No.: 16/303,719

(22) PCT Filed: May 23, 2017

(86) PCT No.: PCT/EP2017/062415
§ 371 (c)(1),
(2) Date: Nov. 21, 2018

(87) PCT Pub. No.: WO2017/202847
PCT Pub. Date: Nov. 30, 2017

(65) Prior Publication Data
US 2019/0223738 A1    Jul. 25, 2019

(30) Foreign Application Priority Data
May 25, 2016  (DE) .................... 10 2016 109 694.6

(51) Int. Cl.
*A61B 5/1455* (2006.01)
*A61B 5/024* (2006.01)

(52) U.S. Cl.
CPC ...... *A61B 5/02433* (2013.01); *A61B 5/02427* (2013.01); *A61B 5/14552* (2013.01);
(Continued)

(58) Field of Classification Search
CPC ..... A61B 5/0059; A61B 5/0205; A61B 5/024; A61B 5/02433; A61B 5/026;
(Continued)

(56) References Cited

U.S. PATENT DOCUMENTS 5,421,329 A    6/1995  Cascani et al.
5,490,506 A *  2/1996  Takatani .............. A61B 5/0059
                                                    356/41
(Continued)

FOREIGN PATENT DOCUMENTS

CN    105266759 A    1/2016
DE    695 33 927    6/2005
(Continued)

OTHER PUBLICATIONS

Notice of Reasons for Rejection dated Jun. 2, 2020, of counterpart Japanese Application No. 2018-557844, along with an English translation.
(Continued)

*Primary Examiner* — Chu Chuan Liu
(74) *Attorney, Agent, or Firm* — DLA Piper LLP (US)

(57) ABSTRACT

A sensor device includes a first light emitter that emits light with a wavelength from a first spectral range, a second light emitter that emits light with a wavelength from a second spectral range, a first light detector configured to detect light with a wavelength from the first spectral range, but not to respond to light with a wavelength from the second spectral range, and a second light detector configured to detect light with a wavelength from the first spectral range and light with a wavelength from the second spectral range, wherein a distance between the first light emitter and the first light detector is smaller than a distance between the second light emitter and the second light detector.

19 Claims, 1 Drawing Sheet

(52) U.S. Cl.
CPC .............. *A61B 2562/0238* (2013.01); *A61B 2562/0242* (2013.01); *A61B 2562/06* (2013.01)

(58) Field of Classification Search
CPC .............. A61B 5/1455; A61B 5/14551; A61B 5/14552; A61B 5/14553; A61B 2562/0238; A61B 2562/0242
See application file for complete search history.

(56) References Cited

U.S. PATENT DOCUMENTS

| | | | |
|---|---|---|---|
| 5,551,422 A | 9/1996 | Simonsen et al. | |
| 5,676,143 A | 10/1997 | Simonsen et al. | |
| 5,830,137 A * | 11/1998 | Scharf | A61B 5/14552 600/323 |
| 6,064,898 A * | 5/2000 | Aldrich | A61B 5/14532 600/316 |
| 8,320,981 B1 * | 11/2012 | Mayer | A61B 5/14503 600/310 |
| 8,945,018 B2 * | 2/2015 | Sankai | A61B 5/0261 600/504 |
| 10,201,287 B2 | 2/2019 | Narusawa et al. | |
| 2001/0005774 A1 | 6/2001 | Kato et al. | |
| 2011/0112387 A1 * | 5/2011 | Li | A61B 5/14551 600/324 |
| 2013/0030267 A1 * | 1/2013 | Lisogurski | A61B 5/14553 600/324 |
| 2015/0057511 A1 | 2/2015 | Basu | |
| 2015/0094550 A1 | 4/2015 | Karp et al. | |
| 2015/0230743 A1 | 8/2015 | Silveira et al. | |
| 2015/0335274 A1 | 11/2015 | Chang et al. | |
| 2016/0345880 A1 * | 12/2016 | Nakaji | A61B 5/14552 |
| 2017/0027459 A1 | 2/2017 | Shimuta et al. | |
| 2017/0325729 A1 | 11/2017 | Halbritter et al. | |

FOREIGN PATENT DOCUMENTS

| | | |
|---|---|---|
| DE | 10 2014 117 879 | 6/2016 |
| JP | 3396222 B2 | 4/2003 |
| JP | 2014-166215 A | 9/2014 |
| JP | 2015-188496 A | 11/2015 |
| WO | 2003/039326 | 5/2003 |
| WO | 2006/094215 A1 | 9/2006 |
| WO | 2007/035934 A2 | 3/2007 |
| WO | 2012/166254 A1 | 12/2012 |
| WO | 2015/109005 | 7/2015 |
| WO | 2015/159692 | 10/2015 |
| WO | 2016/010481 | 1/2016 |
| WO | 2016/111696 | 7/2016 |

OTHER PUBLICATIONS

Notice of Reasons for Rejection dated Jan. 26, 2021, of counterpart Japanese Application No. 2018-557844, along with an English translation.
First Office Action dated Nov. 24, 2020, of counterpart Chinese Application No. 201780032038,9, along with an English translation.
Notice of Reasons for Rejection dated Nov. 19, 2019, of counterpart Japanese Application No. 2018-557844, along with an English translation.

* cited by examiner

SENSOR DEVICE

TECHNICAL FIELD

This disclosure relates to a sensor device.

BACKGROUND

Sensor devices that capture data relevant to the health and fitness of a human user are known. By way of example, such sensor devices can establish a heart rate and/or an arterial oxygen saturation. Methods of capturing such parameters optically by way of measuring light absorption when shining through the skin of the user are known.

SUMMARY

We provide a sensor device including a first light emitter that emits light with a wavelength from a first spectral range, a second light emitter that emits light with a wavelength from a second spectral range, a first light detector configured to detect light with a wavelength from the first spectral range, but not to respond to light with a wavelength from the second spectral range, and a second light detector configured to detect light with a wavelength from the first spectral range and light with a wavelength from the second spectral range, wherein a distance between the first light emitter and the first light detector is smaller than a distance between the second light emitter and the second light detector.

LIST OF REFERENCE SIGNS

Figure 1:
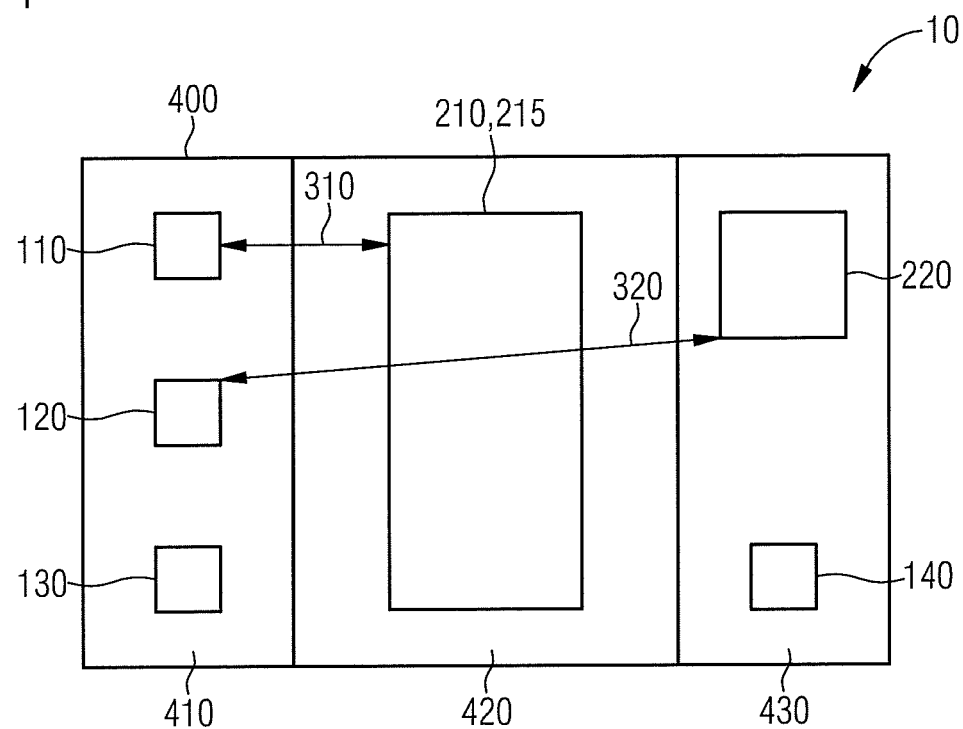
FIG. 1 schematically shows a plan view of a first sensor device.

10 Sensor device
20 Sensor device
110 First light emitter
120 Second light emitter
130 Third light emitter
140 Fourth light emitter
210 First light detector
215 First filter
220 Second light detector
230 Third light detector
235 Further filter
310 First distance
320 Second distance
400 Housing
410 First chamber
420 Second chamber
430 Third chamber

DETAILED DESCRIPTION

Our sensor device comprises a first light emitter that emits light with a wavelength from a first spectral range, a second light emitter that emits light with a wavelength from a second spectral range, a first light detector configured to detect light with a wavelength from the first spectral range, but not to respond to light with a wavelength from the second spectral range, and a second light detector configured to detect light with a wavelength from the first spectral range and light with a wavelength from the second spectral range. A distance between the first light emitter and the first light detector is smaller than a distance between the second light emitter and the second light detector.

The light emitted by the light emitters of this sensor device can be radiated into upper skin layers of the skin of a user of this sensor device. Light reflected at or in the skin of the user can be captured by the light detectors of this sensor device. The first light detector only captures light of the first light emitter while the second light detector is able to capture light of the first light emitter and light of the second light emitter.

Advantageously, the distance between the second light emitter and the associated second light detector in this sensor device is greater than the distance between the first light emitter and the associated first light detector. As a result, the light emitted by the second light emitter travels further in the skin of the user of the sensor device prior to the light's detection by the second light detector than the light emitted by the first light emitter prior to the light's detection by the first light detector. As a result, differences in the degree of reflection and absorption of the light in the skin of the user, which depend on the wavelength of the emitted light, can be taken into account. Advantageously, an increased measurement accuracy of the sensor device may arise herefrom.

As a result of the first light detector configured to only respond to light with a wavelength from the first spectral range, but not to respond to light with a wavelength from the second spectral range, the first light detector can be enabled to detect light with a wavelength from the first spectral range with a particularly high accuracy. By way of example, to this end, the first light detector may comprise a filter that filters out light with a wavelength from the second spectral range, but that lets light with a wavelength from the first spectral range pass.

The sensor device may comprise a third light emitter that emits light with a wavelength from a third spectral range. The first light detector is configured not to respond to light with a wavelength from the third spectral range. The second light detector is configured to detect light with a wavelength from the third spectral range. In this sensor device, light emitted by the third light emitter and reflected at or in the skin of a user of the sensor device is consequently detected by the second light detector, but not by the first light detector. The light emitted by the third light emitter can implement an additional measurement functionality of the sensor device. However, e.g., it also can assist the measurement carried out by the light emitted by the second light emitter. The distance between the third light emitter and the second light detector can likewise be greater than the distance between the first light emitter and the first light detector. As a result of the first light detector not responding to light with a wavelength from the third spectral range, the first light detector can detect light with a wavelength from the first spectral range with a particularly high accuracy.

The third spectral range may be the infrared spectral range. As a result, light emitted by the third light emitter may be suitable, for example, to determine arterial oxygen saturation in the blood of a user of the sensor device by the sensor device.

The first spectral range may be the wavelength range from 520 nm to 570 nm. As a result, light with a wavelength from the first spectral range emitted by the first light emitter may be suitable, for example, to establish a heart rate of a user of the sensor device.

The second spectral range may be the red spectral range. As a result, light with a wavelength from the second spectral range emitted by the second light emitter may be suitable, for example, to establish an arterial oxygen saturation in the blood of a user of the sensor device.

The first light detector may be arranged between the first light emitter and the second light detector. What this advantageously achieves is that a distance between the first light emitter and the first light detector is smaller than a distance between the second light emitter and the second light detector. What arises here is a space-saving arrangement of the components of the sensor device that renders it possible to configure the sensor device in a compact form.

The first light detector may be arranged between the second light emitter and the second light detector. What this also advantageously achieves is that a distance between the first light emitter and the first light detector is smaller than a distance between the second light emitter and the second light detector. What arises here is a space-saving arrangement of the components of the sensor device that renders it possible to configure the sensor device in a compact form.

The sensor device may comprise a fourth light emitter that emits light with a wavelength from the first spectral range. The fourth light emitter can be configured like the first light emitter, for example. Advantageously, this can increase the overall brightness of the light with a wavelength from the first spectral range emitted by the sensor device. Moreover, the first light emitter and the fourth light emitter can be arranged such that the components of the light with a wavelength from the first spectral range emitted by the first light emitter and the fourth light emitter strike the skin of a user of the sensor device from different spatial directions, as a result of which a particularly reliable and accurate measurement can be facilitated.

The first light detector may be arranged between the first light emitter and the fourth light emitter. Advantageously, as a result thereof, components of the light with a wavelength from the first spectral range emitted by the first light emitter and the fourth light emitter shine through different portions of the skin of a user of the sensor device prior to their detection by the first light detector, as a result of which the measurement carried out by the sensor device can be particularly reliable and accurate.

The first light emitter may be arranged between the first light detector and the second light detector. Advantageously, this also represents a space-saving arrangement of the components of the sensor device, in which a distance between the first light emitter and the first light detector is smaller than a distance between the second light emitter and the second light detector. This advantageously facilitates a compact configuration of the sensor device.

The first light emitter may be arranged between the second light emitter and the second light detector. Advantageously, this also represents a space-saving arrangement of the components of the sensor device, in which a distance between the first light emitter and the first light detector is smaller than a distance between the second light emitter and the second light detector. Configuring the sensor device with compact external dimensions is advantageously facilitated thereby.

The sensor device may comprise a third light detector configured to detect light with a wavelength from the first spectral range, but not to respond to light with a wavelength from the second spectral range. Consequently, the third light detector in this sensor device is likewise provided to detect light with a wavelength from the first spectral range emitted by the first light emitter. As a result of the third light detector not responding to light with a wavelength from the second spectral range, the third light detector is allowed to detect light with a wavelength from the first spectral range with a particularly high accuracy. By way of example, to this end, the third light detector may comprise a filter that filters out light with a wavelength from the second spectral range, but does not filter out light with a wavelength from the first spectral range. The first light detector and the third light detector may be arranged in this sensor device such that light emitted by the first light emitter, which is detected by the first light detector, has passed through different portions of the skin of a user of the sensor device than light emitted by the first light emitter, which is detected by the third light detector. This advantageously allows the sensor device to carry out, with a particularly high reliability and accuracy, the measurement carried out using the light emitted by the first light emitter.

The first light emitter may be arranged between the first light detector and the third light detector. As a result, light with a wavelength from the first spectral range emitted by the first light emitter passes through different portions of the skin of a user of the sensor device prior to its detection by the first light detector than prior to its detection by the third light detector. The light emitted by the first light emitter also strikes the skin of a user of the sensor device from different spatial directions. This advantageously allows the sensor device to carry out, with a particularly high reliability and accuracy, the measurement carried out using the light emitted by the first light emitter.

The first light detector may comprise a filter configured to filter out light with a wavelength from the second spectral range. Advantageously, this allows the first light detector to detect light with a wavelength from the first spectral range with a particularly high accuracy without light with a wavelength from the second spectral range, which may strike the first light detector, leading to a disturbance in the measurement signal.

The first light emitter may be configured as a light-emitting diode chip. As an alternative or in addition thereto, the second light emitter can be configured as a light-emitting diode chip. Advantageously, this facilitates a cost-effective and compact example of the light emitters of the sensor device. Moreover, light emitters configured as light-emitting diode chips may be configured to emit light with a very precisely set wavelength.

The first light detector may be configured as a photodetector, in particular as a photodiode. As an alternative or in addition thereto, the second light detector can be configured as a photodetector, in particular as a photodiode. Advantageously, as a result thereof, the light detectors of the sensor device can be configured to be compact, can be obtainable in a cost-effective manner and can facilitate a detection of light with a high accuracy.

The sensor device may be configured to measure a heart rate according to the method of reflective photoplethysmography. Advantageously, the sensor device thereby facilitates an optical measurement of the heart rate without a user of the sensor device having to apply further electrodes or the like to this end.

The sensor device may be configured to measure an oxygen saturation in the blood of a patient. Advantageously, the sensor device here facilitates an optical and non-invasive measurement of the oxygen saturation.

The above-described properties, features and advantages and the manner in which they are achieved will become clearer and more easily understandable in conjunction with the following description of examples explained in more detail in conjunction with the drawings.

FIG. 1 shows a plan view of a schematically illustrated sensor device 10 according to a first example. The sensor device 10 is provide to establish data relevant to the health or fitness of a user of the sensor device 10. By way of example, the sensor device 10 can be provided to measure an arterial oxygen saturation in the blood of a user of the sensor device 10. Additionally, the sensor device 10 can be provided to establish a heart rate (pulse frequency) of a user of the sensor device 10 according to the method of reflective photoplethysmography. The measurements undertaken by the sensor device 10 are carried out here by optical methods.

The sensor device 10 comprises a housing 400, which is only illustrated schematically in FIG. 1. FIG. 1 shows a plan view of an upper side of the housing 400. The housing 400 may comprise a cover (not shown in FIG. 1) on its upper side. Should such a cover be present, the latter is at least partly transparent to light that can be emitted by the sensor device 10. By way of example, the sensor device 10 can be integrated into a portable appliance, in particular a wristwatch, for example.

For the purposes of carrying out measurements, the housing 400 of the sensor device 10 must be arranged at the skin of a user of the sensor device 10 such that the upper side of the housing 400 faces the skin of the user.

The sensor device 10 comprises a first light emitter 110. The first light emitter 110 is configured to emit light with a wavelength from a first spectral range. By way of example, the first spectral range can be the wavelength range from 520 nm to 570 nm. The light that can be emitted by the first light emitter 110 has a green color in this case.

Further, the sensor device 10 comprises a second light emitter 120. The second light emitter 120 is configured to emit light with a wavelength from a second spectral range. By way of example, the second spectral range can be the red spectral range. By way of example, the light emitted by the second light emitter 120 can comprise a wavelength of 660 nm.

Additionally, the sensor device 10 comprises a third light emitter 130. The third light emitter 130 is configured to emit light with a wavelength from a third spectral range. By way of example, the third spectral range can be the infrared spectral range. By way of example, the light emitted by the third light emitter 130 can comprise a wavelength of 940 nm.

The sensor device 10 further comprises a fourth light emitter 140. The fourth light emitter 140 is configured to emit light with a wavelength from the first spectral range. The fourth light emitter 140 can be configured to emit light with the same or similar wavelength as the first light emitter 110.

The first light emitter 110, the second light emitter 120, the third light emitter 130 and the fourth light emitter 140 can each be configured as a light-emitting diode chip (LED chip).

Further, the sensor device 10 comprises a first light detector 210. The first light detector 210 is configured to detect light with a wavelength from the first spectral range striking the first light detector 210. Further, the first light detector 210 is configured not to respond to light with a wavelength from the second spectral range striking the first light detector 210. The first light detector 210 does not respond to light with a wavelength from the third spectral range striking the first light detector 210 either. To this end, the first light detector 210 can comprise a first filter 215 configured to filter out light with a wavelength from the second spectral range and light with a wavelength from the third spectral range, but to let light with a wavelength from the first spectral range pass. By way of example, the first filter 215 can be configured as an interference filter, in particular as, e.g., a Bragg mirror.

In addition to the first light detector 210, the sensor device 10 comprises a second light detector 220. The second light detector 220 is configured to detect light with a wavelength from the first spectral range, light with a wavelength from the second spectral range and light with a wavelength from the third spectral range. By way of example, the second light detector 220 can be configured to detect light with any wavelength from a broad wavelength range, which comprises the first spectral range, the second spectral range and the third spectral range.

The first light detector 210 and the second light detector 220 of the sensor device 10 can be, e.g., photodetectors, in particular, e.g., as photodiodes.

The first light emitter 110, the fourth light emitter 140 and the first light detector 210 can determine a heart rate of a user of the sensor device 10 optically by the method of reflective photoplethysmography. To this end, light with a wavelength from the first spectral range emitted by the first light emitter 110 and the fourth light emitter 140 is radiated into upper skin layers of the skin of a user of the sensor device 10. The light with a wavelength from the first spectral range is partly absorbed and partly reflected in the skin of the user. Light with a wavelength from the first spectral range reflected at or in the skin of the user can reach the first light detector 210 and the light is detected by the first light detector 210. Hemoglobin contained in the blood forms a strong absorber in the skin of the user of the sensor device 10. As a result of the heartbeat-dependent change in the volume of the blood vessels in the skin of the user, there is also a change in the amount of the light with a wavelength from the first spectral range reflected, in a heartbeat-dependent manner, in the skin of the user to the first light detector 210. This is detected by the first light detector 210 to establish the heart rate of the user of the sensor device 10.

The light with a wavelength from the first spectral range emitted by the first light emitter 110 and the light with a wavelength from the first spectral range emitted by the fourth light emitter 140 strike the skin of a user of the sensor device 10 from different spatial directions and pass through different portions of the skin on their path to the first light detector 210. As a result, the measurement undertaken by the sensor device 10 can be carried out with a particularly high accuracy and a particularly low susceptibility to errors. It is expedient if the first light detector 210 is arranged between the first light emitter 110 and the fourth light emitter 140 as illustrated in FIG. 1. However, in a simplified example, either the first light emitter 110 or the fourth light emitter 140 can also be dispensed with.

Detection of the light with a wavelength from the first spectral range emitted by the first light emitter 110 and the fourth light emitter 140 that was reflected at or in the skin of a user of the sensor device 10, undertaken by the first light detector 210, is advantageously not disturbed by light with a wavelength from the second spectral range emitted by the second light emitter 120 or by light with a wavelength from the third spectral range emitted by the third light emitter 130 since such light with a wavelength from the second spectral range or from the third spectral range is filtered out by the first filter 215 of the first light detector 210.

The second light emitter 120, the third light emitter 130 and the second light detector 220 of the sensor device 10 can measure an arterial oxygen saturation of a user of the sensor device 10. To this end, light with a wavelength from the second spectral range emitted by the second light emitter 120 and light with a wavelength from the third spectral range emitted by the third light emitter 130 are radiated into the upper skin layers of the skin of a user of the sensor device 10 and there the light is absorbed and reflected in a wavelength-dependent manner. Some of the light with a wavelength from the second spectral range and some of the light with a wavelength from the third spectral range return to the sensor device 10 and strike the second light detector 220, where the light is detected. The arterial oxygen saturation in the blood of the user of the sensor device 10 can be deduced from the amount of the light with a wavelength from the second spectral range reaching the second light detector 220 and the amount of the light with a wavelength from the third spectral range reaching the second light detector 220.

Since the scattering and absorption of light with a wavelength from the second spectral range and of light with a wavelength from the third spectral range in human skin may be less than the scattering and absorption of light with a wavelength from the first spectral range, it is expedient for the purposes of obtaining good measurement results if the light with a wavelength from the first spectral range emitted by the first light emitter 110 and the fourth light emitter 140 travels a shorter distance in the skin of a user of the sensor device 10 than the light with a wavelength from the second spectral range emitted by the second light emitter 120 and the light with a wavelength from the third spectral range emitted by the third light emitter 130. In the sensor device 10, this is achieved by virtue of a first distance 310 between the first light emitter 110 and the first light detector 210 being smaller than a second distance 320 between the second light emitter 120 and the second light detector 220. A distance between the fourth light emitter 140 and the first light detector 210 substantially corresponds to the first distance 310 between the first light emitter 110 and the first light detector 210. Accordingly, a distance between the third light emitter 130 and the second light detector 220 also substantially corresponds to the second distance 320 between the second light emitter 120 and the second light detector 220.

To achieve the desired distances 310, 320 between the light emitters 110, 120, 130, 140 and the light detectors 210, 220 with a space-saving arrangement of the components of the sensor device 10, the first light detector 210 is arranged between the first light emitter 110 and the second light detector 220. Moreover, the first light detector 210 is arranged between the second light emitter 120 and the second light detector 220.

The housing 400 of the sensor device 10 is subdivided into a first chamber 410, a second chamber 420 and a third chamber 430. The second chamber 420 is arranged between the first chamber 410 and the third chamber 430. The chambers 410, 420, 430 are delimited from one another by light-opaque walls.

The first light emitter 110, the second light emitter 120 and the third light emitter 130 are arranged in the first chamber 410 of the housing 400. The first light detector 210 is arranged in the second chamber 420 of the housing 400. The fourth light emitter 140 and the second light detector 220 are arranged in the third chamber 430 of the housing 400. Arranging the light emitters 110, 120, 130, 140 and the light detectors 210, 220 in separate chambers 410, 420, 430 of the housing 400 of the sensor device 10 that are sealed off from one another in a light-opaque manner prevents light emitted by the light emitters 110, 120, 130, 140 from reaching the light detectors 210, 220 along a direct path without a preceding reflection at or in the skin of a user of the sensor device 10. However, the subdivision of the housing 400 into separate chambers 410, 420, 430 can also be dispensed with.

Figure 2:
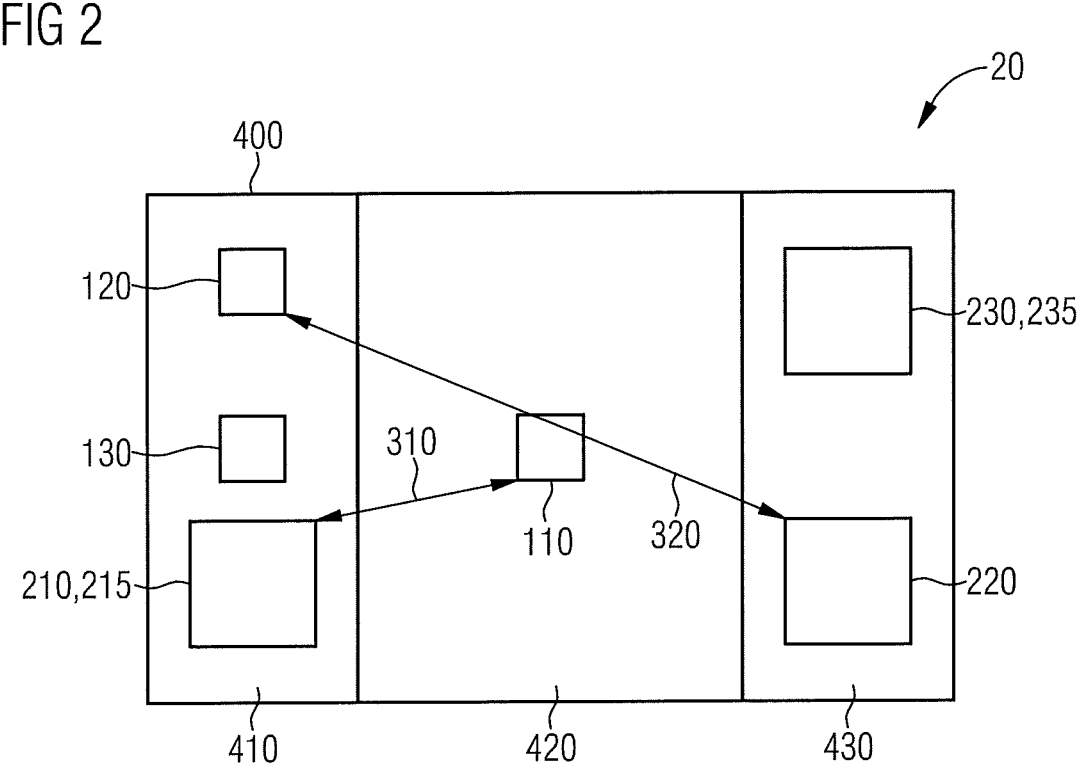
FIG. 2 schematically shows a plan view of a second sensor device.

FIG. 2 shows a plan view of a sensor device 20 according to a second example. The sensor device 20 corresponds to the sensor device 10 to a large extent. Components of the sensor device 20 that correspond to components present in the sensor device 10 are provided with the same reference signs in FIG. 2 as in FIG. 1. Only the differences between the sensor device 20 and the sensor device 10 are described below. Otherwise, the description provided above for the sensor device 10 of FIG. 1 also applies to the sensor device 20 of FIG. 2.

The sensor device 20 only comprises the first light emitter 110 for emitting light with a wavelength from the first spectral range. It lacks the fourth light emitter 140.

Instead, the sensor device 20 comprises a third light detector 230 in addition to the first light detector 210 and the second light detector 220. The third light detector 230 is configured to detect light with a wavelength from the first spectral range, but not to respond to light with a wavelength from the second spectral range and light with a wavelength from the third spectral range. To this end, the third light detector 230 may comprise a further filter 235, which is configured to filter out light with a wavelength from the second spectral range and light with a wavelength from the third spectral range, but to let light with a wavelength from the first spectral range pass. The third light detector 230 can be configured like the first light detector 210. The further filter 235 of the third light detector 230 can be configured like the first filter 215 of the first light detector 210.

The first light emitter 110, the first light detector 210 and the third light detector 230 of the sensor device 20 can measure the heart rate of a user of the sensor device 10. To this end, both the first light detector 210 and the third light detector 230 detect light with a wavelength from the first spectral range emitted by the first light emitter 110, the light having been reflected at or in the skin of a user of the sensor device 10. Light with a wavelength from the first spectral range detected by the first light detector 210 in this case passes through different portions of the skin of the user of the sensor device 10 than light with a wavelength from the first spectral range detected by the third light detector 230. The light detected by the first light detector 210 also struck the skin of the user of the sensor device from a different spatial direction than the light with a wavelength from the first spectral range detected by the third light detector 230. As result, the heart rate can also be measured with high accuracy and low susceptibility to errors in the sensor device 20.

It is expedient if the first light emitter 110 is arranged between the first light detector 210 and the third light detector 230, as in the example shown in FIG. 2. A space-saving arrangement of the components of the sensor device 20 arises if the first light emitter 110 is arranged between the first light detector 210 and the second light detector 220 and the first light emitter 110 is moreover arranged between the second light emitter 120 and the second light detector 220, as shown in FIG. 2. This can be achieved by virtue of the first light emitter 110 being arranged in the second chamber 420 of the housing 400, the second light emitter 120, the third light emitter 130 and the first light detector 210 being arranged in the first chamber 410 of the housing 400 and the second light detector 220 and the third light detector 230 being arranged in the third chamber 430 of the housing 400.

This arrangement also ensures that, in the sensor device 20, the first distance 310 between the first light emitter 110 and the first light detector 210 is smaller than the second distance 320 between the second light emitter 120 and the second light detector 220. The distance between the third light emitter 130 and the second light detector 220 again approximately corresponds to the second distance 320 between the second light emitter 120 and the second light detector 220. The distance between the first light emitter 110 and the third light detector 230 approximately corresponds to the first distance 310 between the first light emitter 110 and the first light detector 210.

Our sensors are described and illustrated more closely on the basis of preferred examples. Nevertheless, this disclosure is not restricted to the disclosed examples. Rather, other variations can be derived therefrom by those skilled in the art without departing from the scope of protection of the appended claims.

This application claims priority of DE 10 2016 109 694.6, the subject matter of which is incorporated herein by reference.

The invention claimed is:

1. A sensor device comprising:
   a housing subdivided into a first chamber, a second chamber and a third chamber, wherein the second chamber is arranged between the first chamber and the third chamber, and the first, second and third chambers are delimited from one another by light-opaque walls,
   a first light emitter that emits light with a wavelength from a first spectral range,
   a second light emitter that emits light with a wavelength from a second spectral range,
   a first light detector configured to detect light with a wavelength from the first spectral range, but not to respond to light with a wavelength from the second spectral range, and
   a second light detector configured to detect light with a wavelength from the first spectral range and light with a wavelength from the second spectral range,
   wherein the first light emitter is arranged in the second chamber,
   the second light emitter and the first light detector are arranged in the first chamber,
   the second light detector is arranged in the third chamber of the housing, and
   a distance between the first light emitter and the first light detector is smaller than a distance between the second light emitter and the second light detector.

2. The sensor device according to claim 1, further comprising:
   a third light emitter that emits light with a wavelength from a third spectral range,
   wherein the first light detector is configured not to respond to light with a wavelength from the third spectral range, and
   the second light detector is configured to detect light with a wavelength from the third spectral range.

3. The sensor device according to claim 2, wherein the third spectral range is the infrared spectral range.

4. The sensor device according to claim 1, wherein the first spectral range is the wavelength range of 520 nm to 570 nm.

5. The sensor device according to claim 1, wherein the second spectral range is the red spectral range.

6. The sensor device according to claim 1, wherein the first light detector is arranged between the first light emitter and the second light detector.

7. The sensor device according to claim 1, wherein the first light detector is arranged between the second light emitter and the second light detector.

8. The sensor device according to claim 1, further comprising a fourth light emitter that emits light with a wavelength from the first spectral range.

9. The sensor device according to claim 8, wherein the first light detector is arranged between the first light emitter and the fourth light emitter.

10. The sensor device according to claim 1, wherein the first light emitter is arranged between the first light detector and the second light detector.

11. The sensor device according to claim 1, wherein the first light emitter is arranged between the second light emitter and the second light detector.

12. The sensor device according to claim 1, further comprising a third light detector configured to detect light with a wavelength from the first spectral range, but not to respond to light with a wavelength from the second spectral range.

13. The sensor device according to claim 12, wherein the first light emitter is arranged between the first light detector and the third light detector.

14. The sensor device according to claim 1, wherein the first light detector comprises a filter configured to filter out light with a wavelength from the second spectral range.

15. The sensor device according to claim 1, wherein the first light emitter is configured as a light-emitting diode chip and/or the second light emitter is configured as a light-emitting diode chip.

16. The sensor device according to claim 1, wherein the first light detector is configured as a photodetector or a photodiode, and/or the second light detector is configured as a photodetector or a photodiode.

17. The sensor device according to claim 1, configured to measure a heart rate according to reflective photoplethysmography.

18. The sensor device according to claim 1, wherein the sensor device is configured to measure an oxygen saturation in blood of a patient.

19. A sensor device comprising:
   a housing subdivided into a first chamber, a second chamber and a third chamber, wherein the second chamber is arranged between the first chamber and the third chamber, and the first, second and third chambers are delimited from one another by light-opaque walls,
   a first light emitter that emits light with a wavelength from a first spectral range,
   a second light emitter that emits light with a wavelength from a second spectral range,
   a first light detector configured to detect light with a wavelength from the first spectral range, but not to respond to light with a wavelength from the second spectral range, and
   a second light detector configured to detect light with a wavelength from the first spectral range and light with a wavelength from the second spectral range,
   wherein the first light emitter and the second light emitter are arranged in the first chamber,
   the first light detector is arranged in the second chamber,
   the second light detector is arranged in the third chamber of the housing, and
   a distance between the first light emitter and the first light detector is smaller than a distance between the second light emitter and the second light detector.

* * * * *